United States Patent [19]

Chen et al.

[11] 4,420,561

[45] Dec. 13, 1983

[54] FERMENTATION PROCESS

[75] Inventors: Nai Y. Chen, Titusville; Joseph N. Miale, Lawrenceville, both of N.J.

[73] Assignee: Mobil Oil Corporation, New York, N.Y.

[21] Appl. No.: 230,461

[22] Filed: Feb. 2, 1981

[51] Int. Cl.$^3$ ............................................. C12P 7/06
[52] U.S. Cl. ................................. 435/161; 435/244; 435/256; 435/942; 585/408; 585/640
[58] Field of Search ............... 435/161, 255, 311, 256, 435/244, 801, 247, 942; 585/408, 640

[56] References Cited

U.S. PATENT DOCUMENTS

| | | |
|---|---|---|
| 2,054,736 | 9/1936 | Boinet . |
| 2,155,134 | 4/1939 | Karsch . |
| 2,371,208 | 3/1945 | Alzola . |
| 2,474,170 | 6/1949 | Sulzbacher ...................... 435/161 X |
| 2,476,785 | 7/1949 | Wallerstein .......................... 435/161 |
| 2,967,107 | 1/1961 | Geiger et al. . |
| 3,000,792 | 9/1961 | Denkewalter et al. ................ 435/75 |
| 3,015,612 | 1/1962 | Pirt et al. . |
| 3,022,225 | 2/1962 | Colin . |
| 3,078,166 | 2/1963 | Hough et al. . |
| 3,117,005 | 1/1964 | Coutts . |
| 3,201,328 | 8/1965 | Williams . |
| 3,207,605 | 9/1965 | Pollock . |
| 3,207,606 | 9/1965 | Williams . |
| 3,219,319 | 11/1965 | Ash . |
| 3,234,026 | 2/1966 | Coutts . |
| 3,413,124 | 11/1968 | Akin . |
| 3,528,889 | 9/1970 | Portno . |
| 3,551,297 | 12/1970 | Hosler ............................. 435/311 X |
| 3,575,813 | 4/1971 | Rothmayr . |
| 3,702,886 | 11/1972 | Argauer et al. ..................... 423/328 |
| 3,705,841 | 12/1972 | Lumb et al. . |
| 3,709,979 | 1/1973 | Chu . |
| 3,737,323 | 8/1971 | Berdelle-Hilge . |
| 3,832,449 | 8/1974 | Rosinski et al. . |
| 3,845,218 | 10/1974 | Mussel . |
| 3,894,107 | 7/1975 | Butter et al. ..................... 585/640 X |
| 3,897,303 | 7/1975 | Sherk et al. ......................... 435/247 |
| 3,898,959 | 8/1975 | Chen et al. ......................... 435/311 |
| 3,928,483 | 12/1975 | Chang et al. .................. 585/408 X |
| 3,940,492 | 2/1976 | Ehnstrom . |
| 4,035,430 | 7/1977 | Dwyer et al. . |
| 4,046,859 | 9/1977 | Plank et al. . |
| 4,138,440 | 2/1979 | Chang et al. . |
| 4,138,442 | 2/1979 | Chang et al. . |
| 4,148,835 | 4/1979 | Chen et al. . |
| 4,156,698 | 5/1979 | Dwyer et al. . |

*Primary Examiner*—R. B. Penland
*Attorney, Agent, or Firm*—Alexander J. McKillop; Michael G. Gilman; Laurence P. Hobbes

[57] ABSTRACT

In an ethanol fermentation process in which an aqueous solution of fermentable sugar is converted by an ethanol-producing microorganism such as a yeast to a dilute aqueous solution of ethanol with the ethanol being present in the solution at a concentration which does not exceed a predetermined maximum level, an improvement is provided which comprises selectively sorbing ethanol present in the solution within a hydrophilic crystalline aluminosilicate ZSM-5 or HZSM-5 zeolite so that the non-sorbed ethanol present in the solution does not exceed the predetermined maximum level of concentration therein, and thereafter removing sorbed ethanol from the zeolite.

10 Claims, 1 Drawing Figure

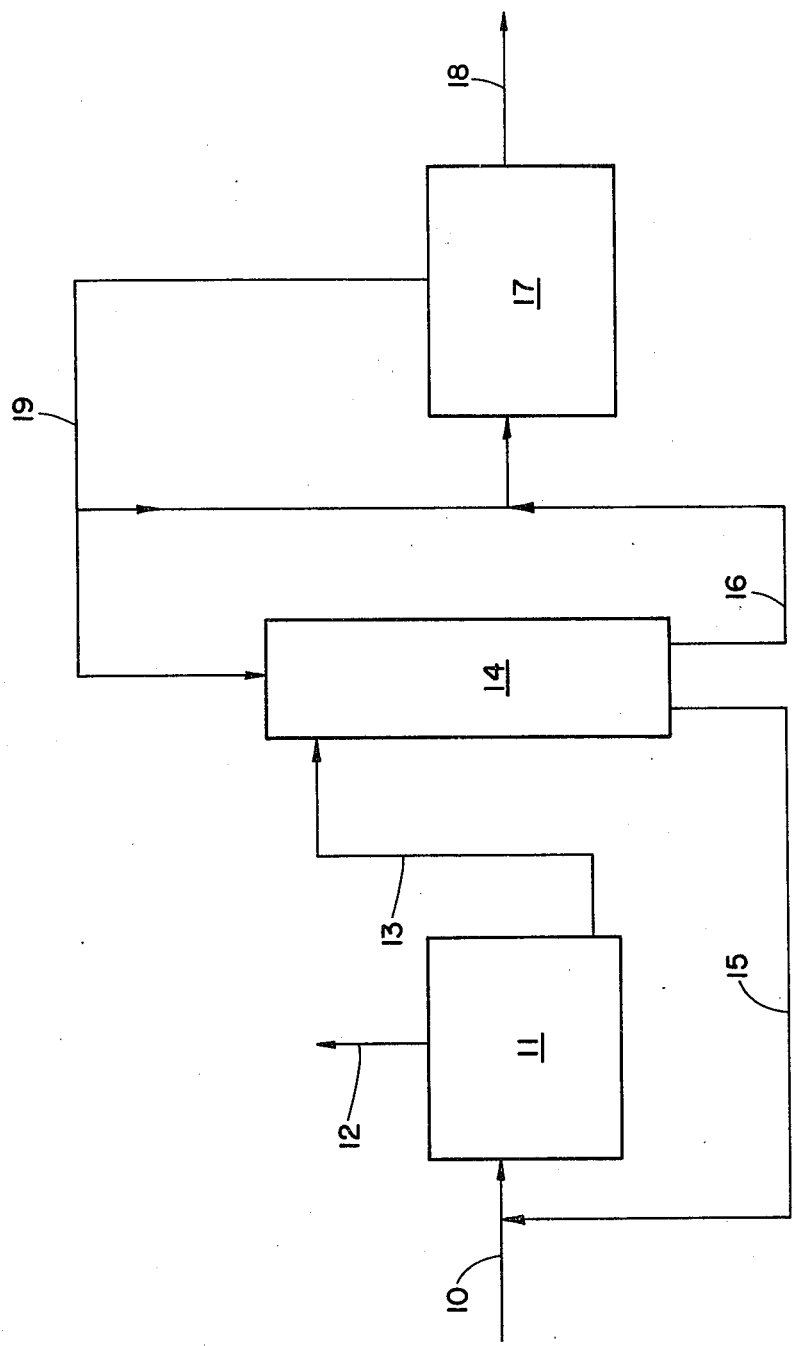

ns are subject, as previously stated, to deterioration in performance (conversion rates) with increasing ethanol levels. Inability to tolerate ethanol concentrations greater than about 10–12% by weight of aqueous fermentation medium has been a long-standing problem which is advantageously overcome by the process of this invention.

FERMENTATION PROCESS

BACKGROUND OF THE INVENTION

1. Field of the Invention

This invention belongs to the field of fermentation processes and, more particularly, to the fermentative conversion of sugars derived from such sources as grains, tubers, starch legumes, sugar cane, agricultural wastes, municipal wastes, wood, sawdust, bark, and the like, to ethanol.

2. Description of the Prior Art

In recent years, considerable attention has been given to the conversion of biomass to liquid fuels and chemicals. Biomass offers the potential to replace or supplement dwindling reserves of non-renewable fossil fuels with fuels derived from vegetative, and therefore, renewable, carbon-containing sources such as amylaceous grains and tubers, sugar cane, wood and other cellulosic sources including cellulose-containing municipal wastes (newsprint, cardboard, etc.), and similar materials. The carbohydrate contained in the foregoing materials is first hydrolyzed to fermentable sugar such as glucose (dextrose), fructose, maltose and sucrose, and the fermentable sugar is thereafter converted by fermentation to ethanol. Hydrolysis and fermentation can be carried out in individual vessels or side-by-side in a single vessel. It is well known that the maximum concentration of ethanol which can be achieved by fermentation is limited by the tolerance of the ethanol-producing microorganisms, e.g., brewers' yeast, Clostridium sp., etc., for ethanol such that as the concentration of the ethanol increases, the ability of the microorganisms to convert further quantities of fermentable sugar to ethanol decreases. At ethanol concentrations above 2% by weight of the fermentation medium, the rate of fermentation begins to decline noticeably with the fall-off in production being particularly apparent when the 5% level has been exceeded. At ethanol concentrations of about 10–12%, fermentation ceases and so this level of ethanol represents an inherent limitation on the productivity of fermentation processes.

In order to achieve maximum production of ethanol from a given volume of fermentation equipment, it is desirable to limit the concentration of ethanol in the fermenter to no higher than about 5%, and preferably, no higher than about 2%. With current fermentation procedures, this has been impractical since it requires processing unacceptably large quantities of liquid. It has been proposed to operate fermenters under vacuum so that the ethanol will volatilize as soon as it is produced thereby making it possible to maintain a low concentration of ethanol in an on-going fermentation. However, vacuum fermentation equipment is expensive to fabricate, use and maintain and its commercial practicality has therefore yet to be established.

SUMMARY OF THE INVENTION

In accordance with the present invention, in an ethanol fermentation process in which an aqueous solution of fermentable sugar is converted by an ethanol-producing microorganism to a dilute aqueous solution of ethanol with the ethanol being present in the solution at a concentration which does not exceed a predetermined maximum level, an improvement is provided which comprises selectively sorbing ethanol present in the solution within a hydrophobic crystalline aluminosilicate zeolite so that the non-sorbed ethanol present in the solution does not exceed the predetermined maximum level of concentration therein, and thereafter desorbing sorbed ethanol from the zeolite.

Employing the process of this invention, it is possible to carry out the fermentative conversion of fermentable sugar to ethanol while maintaining the low concentrations of ethanol which are conducive to optimum rates of ethanol production.

The economy and efficiency with which fermentation ethanol is produced herein makes such ethanol a particularly attractive starting material for conversion to hydrocarbons including gasoline boiling range products employing crystalline aluminosilicate zeolite catalysts. Conversion processes of this type have been the subject of numerous prior-art disclosures. For example, U.S. Pat. No. 3,928,483 discloses a process for the production of aromatic rich gasoline boiling range hydrocarbons from lower alcohols such as methanol, ethanol, propanol and corresponding ethers. The process is carried out in two or more stages wherein the alcohol or ether is contacted with a condensation catalyst to produce aliphatic dehydration products and water. The dehydration product is thereafter converted to gasoline boiling hydrocarbons by contact with a crystalline aluminosilicate zeolite providing a silica-to-alumina ratio greater than 12, a constraint index, as hereinafter defined, within the range of 1 to 12 and a pore dimension greater than 5 Angstroms. Other U.S. patents describing related conversion processes include U.S. Pat. Nos. 3,894,107; 4,138,442; 4,138,440; and, 4,035,430. Others include U.S. Pat. No. 3,979,472 which discloses the utilization of a modified zeolite catalyst comprising the zeolite material in admixture with an antimony compound. U.S. Pat. No. 4,148,835 discloses the methanol conversion reaction in the presence of a zeolite containing a Group 2B and a Group VIII metal and magnesium; while U.S. Pat. No. 4,156,698 discloses employing an improved rare-earth containing zeolite catalyst in the conversion process. Each of the U.S. patents referred to above are incorporated by reference herein.

Since the class of zeolite catalysts which is useful in the processes of the foregoing U.S. patents include the very same class of zeolites which is useful in the selective sorption of ethanol from dilute aqueous fermentation media according to this invention, and since the by-product gases resulting from the catalytic conversion of ethanol to gasoline in such prior processes provide a convenient vehicle for desorbing sorbed ethanol from the zeolite and carrying the desorbed ethanol to the catalytic reactor for conversion to gasoline, the process herein when coupled with any of the known hydrocarbon conversion processes offers a valuable overall route to the conversion of biomass to motor fuels and other useful products.

DESCRIPTION OF THE PREFERRED EMBODIMENTS

Processes by which fermentable sugar can be converted to ethanol under the action of ethanol-producing microorganisms are well known and consequently do not constitute a part of the invention per se. Illustrative of batch fermentation processes which can be used in the practice of this invention are those described in U.S. Pat. Nos. 2,054,736; 3,022,225; and 3,845,218, each of which is incorporated by reference herein. Fermentation processes of the continuous type and/or apparatus suitable therefor which can be employed in this invention include those described in U.S. Pat. Nos. 2,155,134; 2,371,208; 2,967,107; 3,015,612; 3,078,166; 3,177,005; 3,201,328; 3,207,605; 3,207,606; 3,219,319; 3,234,026; 3,413,124; 3,528,889; 3,575,813; 3,705,841; 3,737,323; and 3,940,492, each of which is incorporated by reference herein.

In the preferred practice of the invention, the concentration of aqueous ethanol in the fermentation zone is maintained at a level which does not exceed a predetermined maximum level, preferably not in excess of about 5% by weight of the aqueous solution, and more preferably, not in excess of about 2% by weight of the aqueous solution, by intermittently or continuously withdrawing a portion of aqueous ethanol from the fermentation zone before the concentration of ethanol therein has exceeded the given maximum level, contacting the portion of aqueous ethanol so withdrawn with a hydrophobic crystalline aluminosilicate zeolite as hereinafter more fully described to effect sorption of ethanol within the zeolite and thereafter desorbing the ethanol from the zeolite, preferably by stripping the ethanol from the zeolite at elevated temperature with a gas which is inert under process conditions.

The crystalline aluminosilicate zeolites herein constitute an unusual class of natural and synthetic minerals. They are characterized by having a rigid crystalline framework structure composed of an assembly of silicon and aluminum atoms, each surrounded by a tetrahedron of shared oxygen atoms, and a precisely defined pore structure. Exchangeable cations are present in the pores.

The preferred zeolite sorbants of this invention are selected from a recently discovered novel and special class of zeolites with unusual properties. These zeolites are also known to induce profound transformations of aliphatic hydrocarbons to aromatic hydrocarbons in commercially desirable yields and are generally highly effective in alkylation, isomerization, disproportionation and other reactions involving aromatic hydrocarbons.

An important characteristic of the crystal structure of this class of zeolites is that it provides constrained access to, and egress from, the intra-crystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred zeolites useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having ratios of from about 50 to about 100 and even higher. Thus, zeolites having a silica to alumina ratio of 10,000 or more are entirely useful ethanol sorbants. The foregoing zeolites possess an intracrystalline sorption capacity for ethanol which is greater than that for water, i.e., they exhibit "hydrophobic" properties. This hydrophobic character is essential to the present invention as it permits the zeolites to selectively sorb ethanol from dilute aqueous solutions. In general, hydrophobicity, and therefore selectivity for ethanol, increases with an increase in the silica to alumina ratio. However, countering such increase in selectivity is an accompanying decrease in sorption capacity and sorption rate and an increase in equilibration time, i.e., the time required to sorb a maximum quantity of ethanol. Accordingly, the choice of zeolite employed herein will depend in part upon the purpose to which the sorbed ethanol will ultimately be put. If, for example, the ethanol (following desorption) is to be converted to ethylene and/or other light olefins employing known conversion procedures, the use of a zeolite having a relatively low silica to alumina ratio which sorbs ethanol at a relatively low ratio, but with short equilibration times, could be more economical than the use of a zeolite having a relatively high silica to alumina ratio since olefin conversion operates satisfactorily with ethanol feed streams of low concentration. If, however, conversion of the ethanol to gasoline and/or aromatics is desired, a zeolite of relatively high silica to alumina ratio could be considered the preferred candidate since known gasoline/aromatic conversion processes favor the use of ethanol feeds of relatively high ethanol concentration.

The class of preferred zeolites herein is exemplified by ZSM-5, ZSM-11, ZSM-12, ZSM-21, and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

The class of preferred zeolites herein is exemplified by ZSM-5, ZSM-11, ZSM-12, ZSM-21, and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

Evidence has been adduced which suggests that ZSM-21 may be composed of at least two different zeolites designated ZSM-35 and ZSM-38, one or both of which are the effective material insofar as the catalysis of this invention is concerned. ZSM-35 is described in U.S. Pat. No. 4,016,245 and ZSM-38 is described in U.S. Pat. No. 4,046,859.

The specific zeolites described, when prepared in the presence of organic cations, lack significant sorptive capability, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this special type of zeolite. More generally, it is desirable to activate this type zeolite by base exchange with ammonium salts followed by calcination in air at about 1000° F. for from about 15 minutes to about 24 hours.

Natural zeolites may sometimes be converted to this type zeolite by various activation procedures and other treatments such as base exchange, steaming, alumina extraction and calcination, alone or in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12 and ZSM-21, with ZSM-5 particularly preferred.

The zeolites used as sorbents in this invention may be in the hydrogen form (indicated by the prefix letter H as in H-ZSM-5) or they may be base exchanged or impregnated to contain ammonium or a metal cation complement. It is desirable to calcine the zeolite after base exchange. The metal cations that may be present include any of the cations of the metals of Groups I through VIII of the periodic table.

Following sorption of ethanol from the dilute aqueous fermentation medium, the ethanol is removed, or desorbed, from the zeolite preferably in a stripping operation employing a gas which is inert to ethanol. Fermentation produces fairly large quantities of carbon dioxide gas which can be effectively employed in stripping sorbed ethanol from the zeolite. Other useful gases include nitrogen, steam, by-product gas from a hydrocarbon conversion reactor (e.g., a mixture of hydrogen, methane and ethane), and the like. The last mentioned gas is especially preferred when the desorbed ethanol is to undergo conversion to hydrocarbons since such gas, in addition to serving as a carrier medium for the ethanol feed, also serves to remove heat generated in the converter and to use this heat in the desorption step. One such conversion process which is particularly preferred for use with the present invention is the gasoline hydrocarbon process of U.S. Pat. No. 3,928,483 which is incorporated by reference herein.

Briefly described, ethanol is converted in accordance with U.S. Pat. No. 3,928,483 to gasoline boiling-range hydrocarbons which can be made to contain greater or lesser quantities of aromatic components depending upon the specific process conditions selected. In the first stage, the ethanol is contacted with a dehydration catalyst to produce water and a predominantly aliphatic organic intermediate product which is largely olefins. In the last stage, the intermediate product, with or without further modification, is contacted with a crystalline aluminosilicate zeolite catalyst having a silica to alumina ratio of at least 12 and a constraint index of 1 to 12 as defined below to convert the intermediate product to a final product which may contain water. The organic portion of this final product is a hydrocarbon mixture having a preponderance of normally fluid hydrocarbon constituents and as previously stated can contain substantial quantities of aromatics, in the gasoline boiling-range of up to 415° F. The reactor effluent also contains by-product gas which is advantageously used to desorb fermentation ethanol as previously described.

Another conversion process which is readily integrated with the fermentation process herein is described in U.S. Pat. No. 3,894,107, also incorporated by reference herein. According to this process, ethanol is directly contacted with a crystalline aluminosilicate zeolite catalyst having a silica to alumina ratio of at least about 12 and a constraint index of about 1 to 12 at an elevated temperature up to about 1,000° F. under such combination of temperature, pressure and space velocity to effect conversion of the ethanol to organic compounds having a higher carbon to oxygen ratio than ethanol. By-product gas also results from this conversion and can likewise be used to desorb fermentation ethanol in accordance with this invention.

The same zeolites which are used for catalyzing the conversion processes described in aforesaid U.S. Pat. Nos. 3,928,483 and 3,894,107 are also useful in the sorption of fermentation ethanol from dilute aqueous solution as practiced in the present invention. However, the zeolites in their role as catalysts are further characterized as possessing a constraint index of 1 to 12. Catalytically active crystalline aluminosilicate zeolites must provide constrained access to larger molecules. While it is sometimes possible to judge from a known crystal structure whether such constrained access exists, a simple determination of the "constraint index" may be made by passing continuously a mixture of equal weight of normal hexane and 3-methylpentane over a small sample, approximately 1 gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows: Constraint Index = $\log_{10}$ (fraction of n-hexane remaining)/$\log_{10}$ (fraction of 3-methylpentane remaining)

The constraint index approximates the ratio of the cracking rate constants for the ratio of the cracking rate constants for the two hydrocarbons. Zeolites suitable for use as catalysts in the conversion processes of U.S. Pat. Nos. 3,928,483 and 3,892,107 are those having a constraint index from 1.0 to 12.0, preferably 2.0 to 7.0, and are advantageously selected from the ZSM-5 and HZSM-5 type zeolites.

The process of the present invention integrated with a process for the conversion of fermentation ethanol to hydrocarbon fuels and chemicals is schematically illustrated in the attached drawing in which a sterile aqueous solution of one or more fermentable sugars obtained from the hydrolysis of carbohydrate derived from biomass is introduced through line 10 to a fermenter 11 containing a yeast such as *Saccharomyces cerevisiae*. The dilute aqueous solution of ethanol produced in fermenter 11 from which most of the yeast has been removed is withdrawn therefrom through line 13 and introduced to ethanol sorption/desorption unit 14. Carbon dioxide produced during fermentation is vented through line 12. Sorption/desorption unit 14, which contains a zeolite sorption medium, is operated in alternate sorption/desorption cycles. In the sorption cycle, ethanol present in the dilute aqueous fermentation stream is sorbed into the zeolite. In the desorption cycle, by-product gas from catalytic hydrocarbon converter 17 passing through line 19 is introduced into unit 14 to strip the ethanol from the zeolite, the desorbed ethanol being routed through line 16 together with said by-product gas into converter 17. The ethanol-depleted aqueous solution in unit 14 is recycled to fermenter 11 through line 15 to dilute the fermentation medium and maintain the ethanol concentration therein at or below a predetermined maximum level. Ethanol is reacted over zeolite catalyst in converter 17 to provide a product hydrocarbon effluent through line 18 and by-product gas through line 19.

The following examples are further illustrative of the process of the present invention.

EXAMPLES 1-2

Two dilute aqueous solutions of ethanol simulating the ethanol-containing effluent from a fermenter were subjected to sorption at room temperature with crystalline aluminosilicate zeolites of the HZSM-5 type followed by desorption at 130° C. The results of the sorptions for each ethanol solution were as follows:

|  | Example 1 | Example 2 |
|---|---|---|
| % by weight ethanol in aqueous solution | 1.98 | 2.49 |
| HZSM-5 approximate silica: alumina ratio | 70 | 50,000 |
| Equilibration Time (hours) | <1 | 48 |
| % by weight ethanol sorbed | 10.94 | 5.89 |
| % by weight ethanol in sorbed phase | 56.7 | 100 |

As these data show, at the higher silica:alumina ratio, selectivity for ethanol was substantially 100% compared with 56.7% for the lower silica:alumina ratio zeolite. However, the reduced sorption capacity and sorption rate of the higher silica:alumina ratio zeolite is evident in the much longer equilibration period for this zeolite compared with the zeolite of lower silica:alumina ratio zeolite.

What is claimed is:

1. In an ethanol fermentation process in which an aqueous solution of fermentable sugar is converted by an ethanol-producing microorganism to carbon dioxide and a dilute aqueous solution of ethanol with the ethanol being present in the solution at a concentration which does not exceed a predetermined maximum level, said predetermined maximum level of ethanol being selected to be that which is below the level of ethanol causing fermentation to substantially cease, the improvement comprising selectively sorbing ethanol present in the solution during fermentation within a hydrophobic crystalline aluminosilicate ZSM-5 or HZSM-5 zeolite possessing a silica to alumina ratio of greater than about 12 so that the non-sorbed ethanol present in the solution does not exceed the predetermined maximum level of concentration therein, and thereafter desorbing sorbed ethanol from the zeolite by stripping said zeolite with the carbon dioxide obtained from the ethanol fermentation process.

2. The process of claim 1 wherein the pedetermined maximum level of ethanol in aqueous solution is about 5% by weight of the solution.

3. The process of claim 1 wherein the predetermined maximum level of ethanol in aqueous solution is about 2% by weight of the solution.

4. The process of claim 1 wherein the hydrophobic crystalline aluminoslicate zeolite possesses a silica to alumina ratio of from about 50 to about 100.

5. The process of claim 1 wherein the hydrophobic crystalline aluminoslicate zeolite possesses a silica to alumina ratio of greater than about 10,000.

6. The process of claim 1 wherein a portion of the dilute aqueous solution of ethanol is intermittently or continuously transferred to a sorption zone for contact with the hydrophobic crystalline aluminosilicate zeolite.

7. An integrated process for converting fermentable sugar in aqueous solution to gasoline boiling range products which comprises:
 (a) converting fermentable sugar present in an aqueous solution thereof under the action of an ethanol-producing microorganism to provide a dilute aqueous solution of ethanol with the ethanol being present in the solution at a concentration which does not exceed a predetermined maximum level, said predetermined maximum level of ethanol being selected to be that which is below the level of ethanol causing fermentation to substantially cease;
 (b) selectively sorbing ethanol present in the dilute aqueous ethanol solution resulting from step (a) during fermentation within a hydrophobic crystalline alumino-silicate ZSM-5 or HZSM-5 zeolite possessing a silica to alumina ratio of greater than about 12;
 (c) desorbing sorbed ethanol from said zeolite by stripping with a carrier gas;
 (d) contacting desorbed ethanol with a dehydration catalyst to provide water and an aliphatic organic intermediate product comprising olefins;
 (e) separating water from said aliphatic organic intermediate product;
 (f) contacting the aliphatic organic intermediate product with a crystalline aluminosilicate ZSM-5 or HZSM-5 zeolite catalyst, said crystalline zeolite characterized by a pore dimension greater than 5 Angstroms, a silica to alumina ratio greater than 12, and a constraint index within the range of 1 to 12, to effect conversion of said aliphatic organic intermediate product to gasoline boiling range products, and by-product gas; and,
 (g) employing the by-product gas resulting from step (f) as carrier gas in desorbing step (c).

8. The process of claim 7 wherein the predetermined maximum level of ethanol in aqueous solution is about 5% by weight of the solution.

9. An integrated process for converting fermentable sugar present in aqueous solution to organic compounds having a higher carbon to oxygen ratio than ethanol which comprises:
 (a) converting fermentable sugar present in an aqueous solution thereof under the action of an ethanol-producing microorganism to provide a dilute aqueous solution of ethanol with the ethanol being present in the solution at a concentration which does not exceed a predetermined maximum level, said predetermined maximum level of ethanol being selected to be that which is below the level of ethanol causing fermentation to substantially cease;
 (b) selectively sorbing ethanol present in the dilute aqueous ethanol solution resulting from step (a) during fermentation within a hydrophobic crystalline aluminosilicate ZSM-5 or HZSM-5 zeolite possessing a silica to alumina ratio of greater than about 12 so that non-sorbed ethanol remaining in said dilute aqueous ethanol solution does not exceed the predetermined maximum level of concentration therein;
 (c) desorbing sorbed ethanol from said zeolite by stripping with a carrier gas;

(d) contacting desorbed ethanol with a crystalline aluminosilicate zeolite catalyst having a silica to alumina ratio of at least about 12 and a constraint index of about 1 to 12 at an elevated temperature up to about 1000° F. under such combination of temperature, pressure and space velocity to effect conversion of the ethanol to organic compounds having a higher carbon to oxygen ratio than ethanol, and by-product gas; and, (e) employing the by-product gas resulting from step (d) as carrier gas in desorbing step (c).

10. The process of claim 9 wherein the predetermined maximum level of ethanol in aqueous solution is about 5% by weight of the solution.

* * * * *